(12) United States Patent
Shimomura et al.

(10) Patent No.: US 10,521,504 B2
(45) Date of Patent: Dec. 31, 2019

(54) METHODS AND APPARATUS FOR OBTAINING A SNAPSHOT OF A MEDICAL IMAGING DISPLAY

(71) Applicants: Takuya Shimomura, Cary, NC (US); Tatsuo Kawanaka, Cary, NC (US)

(72) Inventors: Takuya Shimomura, Cary, NC (US); Tatsuo Kawanaka, Cary, NC (US)

(73) Assignee: FUJIFILM MEDICAL SYSTEMS U.S.A., INC., Morrisville, NC (US)

( * ) Notice: Subject to any disclaimer, the term of this patent is extended or adjusted under 35 U.S.C. 154(b) by 116 days.

(21) Appl. No.: 15/687,245

(22) Filed: Aug. 25, 2017

(65) Prior Publication Data

US 2017/0351412 A1    Dec. 7, 2017

Related U.S. Application Data

(62) Division of application No. 14/736,550, filed on Jun. 11, 2015.

(51) Int. Cl.
| | |
|---|---|
| *G06F 17/24* | (2006.01) |
| *G06F 3/0481* | (2013.01) |
| *G16H 30/40* | (2018.01) |
| *G16H 30/00* | (2018.01) |
| *H04M 1/247* | (2006.01) |
| *G06F 3/048* | (2013.01) |
| *G06F 3/0482* | (2013.01) |
| *H04N 1/00* | (2006.01) |

(52) U.S. Cl.
CPC .......... *G06F 17/248* (2013.01); *G06F 3/0481* (2013.01); *G06F 3/048* (2013.01); *G06F 3/0482* (2013.01); *G16H 30/00* (2018.01); *G16H 30/40* (2018.01); *H04M 1/2474* (2013.01); *H04N 1/00408* (2013.01)

(58) Field of Classification Search
CPC ........ G06F 17/243; G06F 17/25; G06F 17/26; G06F 19/30; G06F 19/32; G06F 19/321; G06F 19/324; G06Q 50/22; G06Q 50/24; G16H 10/60; G16H 30/00; G16H 30/20; G16H 30/40; G16H 70/20
See application file for complete search history.

(56) References Cited

U.S. PATENT DOCUMENTS

| | | | |
|---|---|---|---|
| 5,987,345 A | 11/1999 | Engelmann et al. | |
| 6,434,569 B1 | 8/2002 | Toshimitsu et al. | |
| 7,058,901 B1* | 6/2006 | Hafey ................ | G16H 40/63 715/792 |
| 7,225,131 B1 | 5/2007 | Bangalore et al. | |
| 2006/0080142 A1 | 4/2006 | Hart et al. | |
| 2008/0031503 A1* | 2/2008 | Kanada ................ | G06F 19/321 382/128 |

(Continued)

*Primary Examiner* — Eric J. Bycer

(74) *Attorney, Agent, or Firm* — Womble Bond Dickinson (US) LLP

(57) ABSTRACT

A method comprising, responsive to a selecting event, rendering an interactive display screen of a saved first state of a display layout of a medical information compilation, the interactive display screen comprising first information in a first display area and second information in a second display area, the saved first state comprising a plurality of display attributes of the first information and the second information, wherein the first information and the second information each include one of (i) a medical image, (ii) medical notes, or (iii) a medical record is described.

7 Claims, 6 Drawing Sheets

(56) References Cited

U.S. PATENT DOCUMENTS

| | | |
|---|---|---|
| 2008/0225057 A1 | 9/2008 | Hertzfeld et al. |
| 2008/0256140 A1 | 10/2008 | Lazzaro et al. |
| 2009/0248757 A1 | 10/2009 | Havewala et al. |
| 2011/0135174 A1 | 6/2011 | Vining et al. |
| 2012/0059669 A1* | 3/2012 | Whittenburg .......... G06Q 50/22 705/3 |
| 2012/0131507 A1* | 5/2012 | Sparandara ............ G16H 10/60 715/833 |
| 2013/0093781 A1* | 4/2013 | Suzuki .................. A61B 6/461 345/581 |
| 2013/0159019 A1* | 6/2013 | Reicher ................ G06F 17/243 705/3 |
| 2015/0265233 A1* | 9/2015 | Aoyagi ................ A61B 5/7425 345/635 |
| 2016/0012082 A1 | 1/2016 | Choudhury |
| 2017/0140105 A1* | 5/2017 | Smith ................ G06F 21/6263 |

* cited by examiner

METHODS AND APPARATUS FOR OBTAINING A SNAPSHOT OF A MEDICAL IMAGING DISPLAY

PRIORITY

The present patent application is a divisional of and incorporates by reference the U.S. patent application Ser. No. 14/736,550, titled, "METHODS AND APPARATUS FOR OBTAINING A SNAPSHOT OF A MEDICAL IMAGING DISPLAY" filed on Jun. 11, 2015.

FIELD

Embodiments of the disclosure relate to improving the display of medical images and information relevant to one or more of the displayed medical images. More specifically, embodiments of the disclosure relate to generating a snapshot of one or more states of a display of medical images and the information relevant to the displayed medical images.

GENERAL BACKGROUND

Current medical imaging technology includes the use of medical images such as, among others, x-rays, mammograms, computerized tomography (CT) scans, magnetic resonance images (MRIs), positron emission tomography (PET) scans and ultrasound images. Some medical facilities, such as doctors' offices, dentists' offices, hospitals, etc., may use x-ray illuminators to view physical printouts of medical images. However, medical facilities are beginning to adopt electronic displays for displaying medical images.

As medical facilities adopt electronic displays, medical personnel, such as doctors, nurses or medical technicians, have difficulty accessing a plurality of pieces of medical information at once. Previously, with x-ray illuminators, for example, a plurality of physical x-ray image films may be hung against a backlit screen of an x-ray illuminator. Additionally, medical personnel had the ability to hang other relevant medical information, such as medical records, charts, surgery procedures, etc., in a side-by-side manner with one or more x-rays.

Upon adopting electronic displays to display medical information, medical personnel are required to open a separate display screen for each piece of medical information. This requires the medical personnel explaining the medical information to continually switch amongst the open windows, which is often clumsy and confusing for the medical personnel as well as for the viewer. For example, a doctor may be explaining an injury using a plurality of x-rays to a patient. By switching between the plurality of open windows, one for each x-ray, it is foreseeable that the doctor and patient may become confused, or the patient might not fully understand the injury and the potential treatment options as a result.

However, one advantage of switching to electronic displays is that adjusting viewing properties for one or more medical images has become easier (e.g., attributes of the one more medical images). For example, adjusting the brightness level of an image on a computer for display on the display screen is easier and more convenient than adjusting the light source of an x-ray illuminator. However, when medical personnel adjusts one or more viewing properties (e.g., zoom level, brightness level, contrast level, etc.) of one or more medical images in order to draw a conclusion on the injury and/or treatment required, the medical personnel is required to recall the adjustments the next time the one or more medical images are displayed. For example, when a doctor increases a zoom level and then increases a contrast level on an x-ray in order to determine, for example, that a fracture is present in the ulna of the patient's left hand, the doctor will have to recall the amount of increase in the zoom level and contrast level when illustrating the fracture to the patient or to a surgeon. Additionally, the doctor may also have to recall the arrangement of a second medical image (or other medical information) that was used in drawing a conclusion regarding the fracture and/or possible treatment options. In some instances, a particular viewing arrangement, e.g., a side-by-side comparison of two medical images having different perspectives of an injury wherein one or more of the medical images have had viewing properties adjusted, may be critical in seeing the injury.

Furthermore, relaying information as to how to adjust the viewing properties and a particular arrangement of medical information to medical personnel located remotely from the medical personnel creating the arrangement is very difficult. For example, if a doctor in California is examining a patient with severe head trauma and would like a second opinion of the diagnosis from the foremost expert in head trauma, who happens to be at a hospital in France, it would be very difficult, currently, for the doctor in California to relay information as to how the medical information (images, notes, medical records, etc.) should be arranged and how the viewing properties of one or more of the medical images should be adjusted.

Therefore, it would be advantageous to have a method of generating a display screen that enabled a doctor to save the state of an arrangement of a plurality of pieces of medical information, including the preservation of any adjusted viewing properties, such that the saved state may be easily recalled in the future.

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

BRIEF DESCRIPTION OF THE DRAWINGS

The disclosure may best be understood by referring to the following description and accompanying drawings that are used to illustrate embodiments of the disclosure.

DETAILED DESCRIPTION

Figure 1:
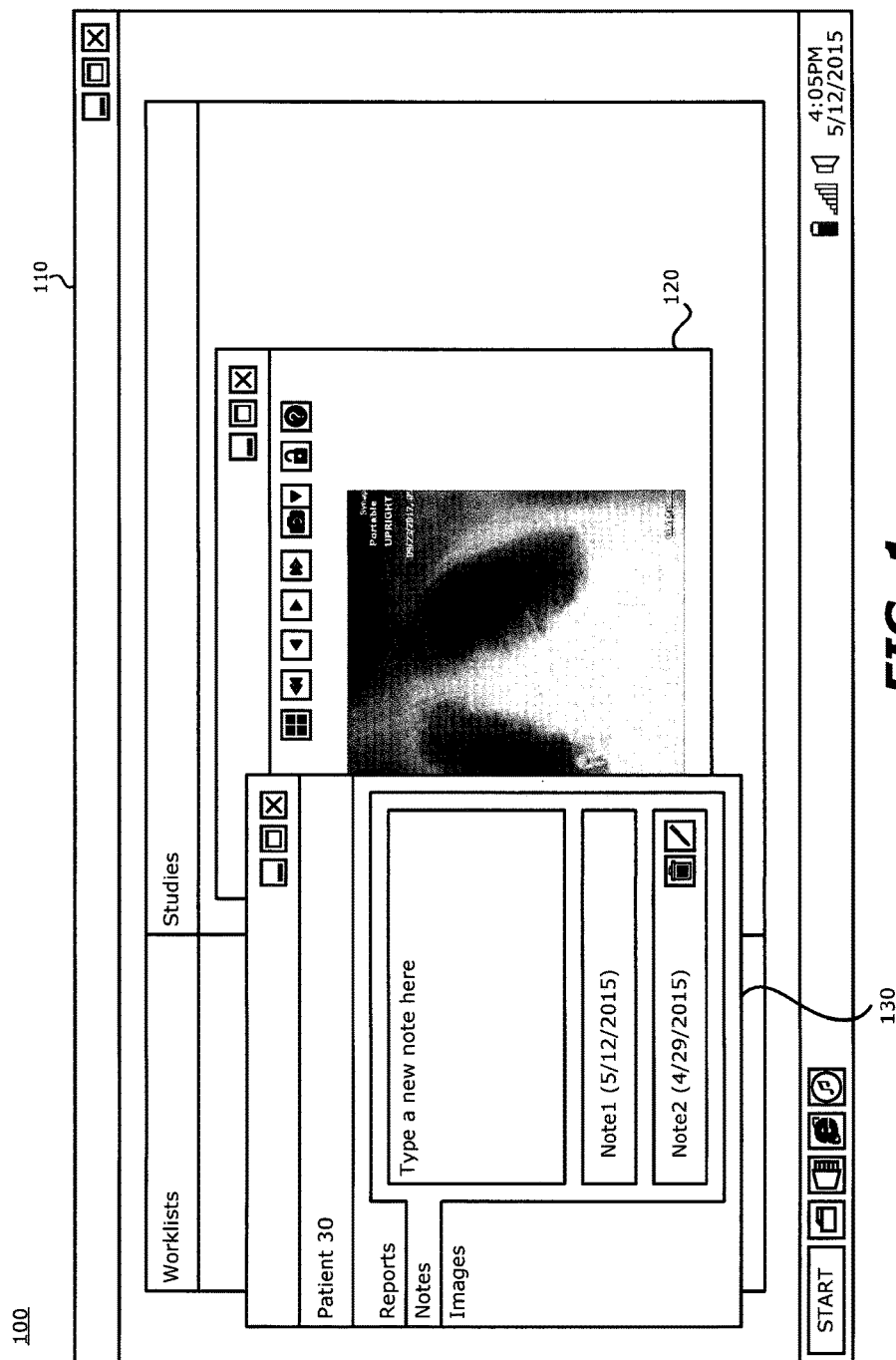
FIG. 1 is a first exemplary embodiment of a plurality of user interactive display screens.

Various embodiments of the disclosure relate to saving the state of one or more user interface screens displaying medical images, and, optionally, information related to one or more of the displayed medical images. One embodiment of a user interface display screen may include a predefined layout comprising one or more medical images, one or more display areas including information pertaining to one or more of the medical images and one or more display areas including information pertaining to a subject of one or more of the medical images (e.g., a patient).

The disclosure is directed to enabling a user (e.g., a medical technician, a nurse and/or a doctor) to select a predefined display layout including a plurality of display areas that divide the layout. Each of the plurality of display areas may include data relevant to a doctor's diagnosis or review of a patient. Alternatively, the data included in the layout may be arranged such that a user may present the data in an organized manner or share the data in the same organized manner with others remotely. Specifically, by enabling a user to save the state of a layout, including the state of each adjusted medical image, the user may quickly recall a particular state of interest that is important to a diagnosis, presentation or is particularly unique. Herein, the term "adjusted image" may refer to a medical image that has had one or more viewing properties altered. Examples of viewing properties may include, but are not limited or restricted to, a zoom level, a brightness level, a contrast level, color settings, a positioning of the image, a rotation of the image, etc.

In one embodiment, several x-rays may be taken of a particular patient from a plurality of angles. A doctor may come to a conclusion as to an injury of the patient and the appropriate procedure to address the injury based on a comparison of two or more x-ray images and the previous medical history of the patient. Therefore, it is desirable for the doctor to be able to save the state of the layout, e.g., the exact layout comparing the two or more x-ray images and the previous medical history, so as to be able to return to the exact layout when discussing the injury or the appropriate procedure with the patient and/or medical staff. Herein, the term "snapshot" may be referred to as a grouping of one or more saved states of a particular layout.

Additionally, a snapshot may be added to a collection or a worklist, as will be discussed below, such that a plurality of snapshots may be grouped together for easy access and viewing. In other embodiments of the disclosure, a snapshot, a collection or a worklist may be shared with others remotely, for example, over a network. For example, a doctor may create a layout and a snapshot may be generated such that the snapshot may be provided to a specialist working at a separate hospital. The specialist may open the snapshot and be presented with the exact layout, including any adjusted images and notes, the doctor who had the snapshot generated. This prevents the specialist from having to manually adjust one or more images or pull up a plurality of screens in order to view the data set including one or more medical images, information relevant to one or more of the medical images and/or information relevant to one or more subjects of one or more of the medical images.

Herein, the term "study" refers broadly to a compilation of medical information that may include a single medical image, a medical record or a set of medical notes, or may include one or more of a medical image, a medical record or a set of medical notes set forth in a design layout (e.g., a template). Additionally, one or more states of the design layout, including the content imported therein and any adjustments made to one or more display attributes, may be saved, wherein the grouping of one or more saved states may be referred to as a snapshot. For example, a first saved state may include a first medical image having a default brightness setting and a second saved state may include the first medical image having an adjusted brightness setting. Each of the one or more saved states may include an adjustment to one or more display attributes of the content of one or more of the display areas. As stated above, the grouping of the one or more saved states of the design layout may be referred to as a snapshot of the design layout.

Referring to FIG. 1, a first exemplary embodiment of a plurality of user interactive display screens is shown. The display 100 includes a plurality of display screens 110, 120 and 130. FIG. 1 illustrates one embodiment of how a user (e.g., a doctor, a medical technician or a nurse) simultaneously views a plurality of medical images and notes relevant to one or more of the medical images or of the subject of one or more of the medical images. The display screen 110 shows a home screen comprising a listing of one or more worklists, one or more collections and one or more studies. The display screen 120 shows a medical image, specifically an x-ray of a chest. Finally, the display screen 130 illustrates a text box for adding notes pertaining to the patient (e.g., "Patient 30") or reviewing previously recording notes.

After reviewing at least the display screens 120 and 130, a user may exit the viewing application (e.g., to take a break, examine another patient, etc.) but may wish to return to the viewing state just prior to exiting the viewing application, or to a particular state of interest. Without implementing the snapshot feature as discussed in this disclosure, the user would be required to open multiple display screens (e.g., the display screens 120 and 130) and adjust the medical image of the display screen 120, if applicable. The user may not be able to recall the steps required to obtain the viewing state just prior to previously exiting, or to obtain the particular state of interest. Therefore, creating a layout with the desired medical images and/or notes and having a snapshot generated would allow the user to quickly recall the state just prior to previously exiting, or recall the particular state of interest.

I. Generation of a Snapshot

Figure 2:
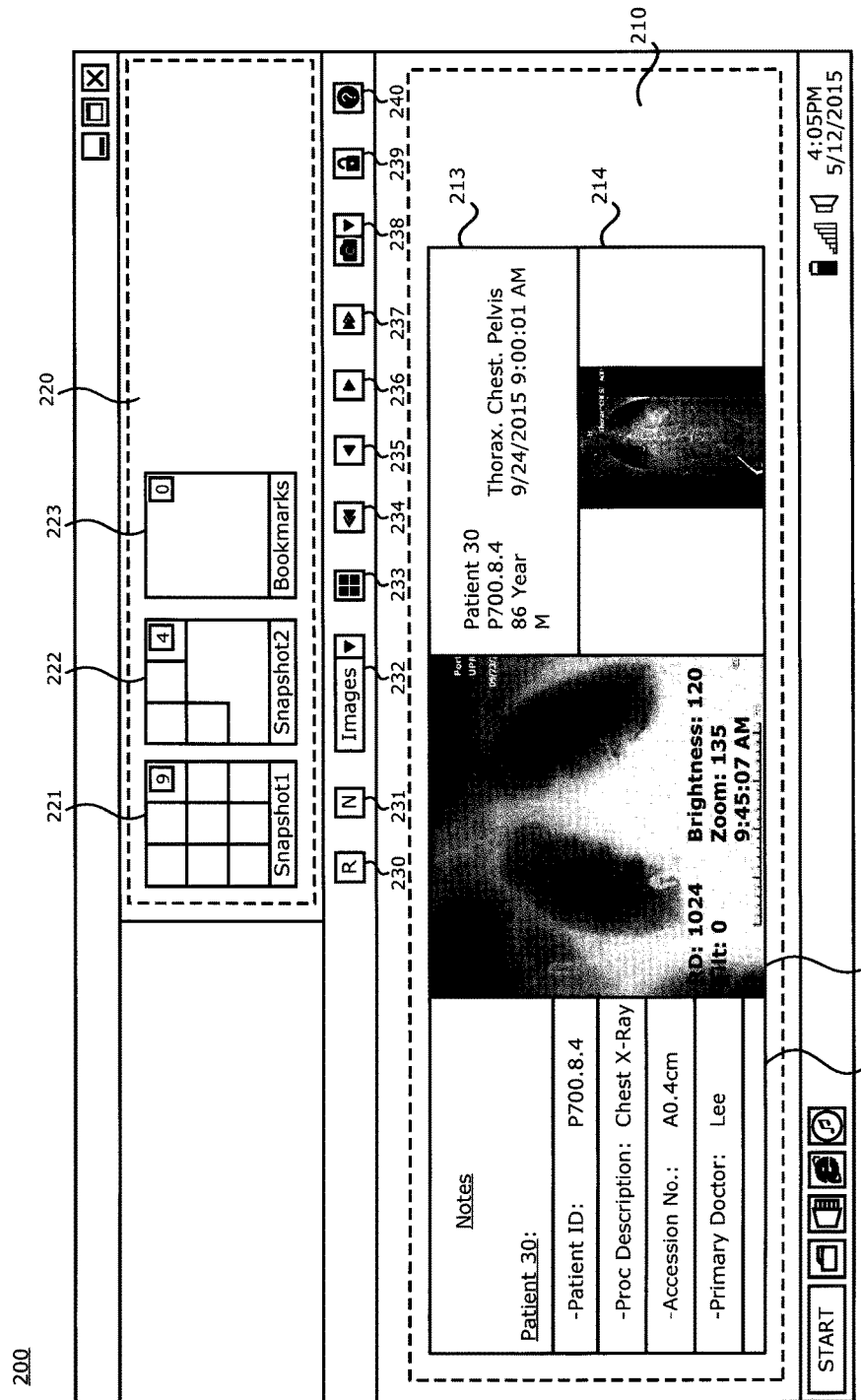
FIG. 2 is an exemplary embodiment of a display screen that illustrates a plurality of display areas, each containing information pertaining to a particular patient.

Referring now to FIG. 2, an exemplary embodiment of a display screen that illustrates a plurality of display areas, each containing information pertaining to a particular patient is shown. Herein, rendered by display control logic, discussed below, the display screen 200 includes a user interactive display screen 210, a history display area 220 and a plurality of icons 230-240 indicating a plurality of actions that may be taken by the viewer. In this embodiment, the user interactive display screen 210 includes four display areas: a notes display area 211, a first medical image 212, a report display area 213 and a second medical image 214. The four display areas 211-214 are set forth in a predefined layout selected by a user. As will be discussed below in accordance with FIG. 3, other layouts may exist other than the layout illustrated in the user interactive display screen 210.

As is seen in the user interactive display screen 210 of FIG. 2, a notes display area 211 may include information relevant to a particular patient, e.g., "Patient 30." The notes display area 211 includes a plurality of examples of patient information that may be included in the notes display area 211 but in other embodiments, more or less information may be included therein. The medical image 212 illustrates one example of a medical image that may be included in a user interactive display screen. The medical image 212 illustrates a first x-ray. As is seen, the medical image 212 may include markings to identify characteristics of the state in which the x-ray was taken (e.g., a brightness level, a zoom level and/or a time). Alternatively, the markings may be used to refer to the adjustment of the medical image 212 once the medical image 212 is placed in a display area of the layout.

The record display area 213 may include information of the subject of the medical images 212 and 214. In the embodiment of FIG. 2, the record display area 213 includes information of the Patient 30, in accordance with the notes display area 211, to provide the viewer one or more pieces of information regarding the subject's age, sex, areas of prior medical issues, etc. As one skilled in the art would recognize, other medical attributes may be provided in the records display areas 213 than just those illustrated herein. The medical image 214 may provide a second perspective of the subject of the subject of the medical image 212. In one embodiment, the medical image 212 may illustrate an x-ray focused on the patient's chest in order to determine whether a lung has been punctured or a rib has been fractured. The medical image 214 may offer the viewer a second perspective of the patient, illustrating an object piercing the patient's body.

In other embodiments, any combination of medical images may be placed within one or more display areas of the layout. For example, a plurality of medical images of a single patient may be placed side by side, similar to the embodiment portrayed as user interactive display screen 210. Alternatively, one or more medical images of a patient's progression from an initial medical image of an injury to a healed state including several medical images taken periodically during recovery. This progression may enable doctors to adequately monitor a patient's recovery. Alternatively, a doctor may want to compare a plurality of medical images of a similar perspective of multiple patients.

The history display area 220 of the display screen 200 may include one or more snapshots that have previously been viewed. For example, the snapshot 221 and the snapshot 222 are illustrative examples of snapshots that may have been viewed previously. Additionally, an icon placed on the snapshot 221 or 222 may be used to indicate the number of states included within the snapshot 221 or 222. In the embodiment of FIG. 2, a numerical icon placed on the snapshot 221 indicates there are nine states within the snapshot 221, similarly an icon indicates there are four states within the snapshot 222. The history display area 200 may also include a "Bookmarks" option 223. The bookmarks option 223 may store links to snapshots, or particular states thereof, for quick access.

The display screen 200 may also include a plurality of icons that a viewer may utilize to invoke various functionalities. In the embodiment illustrated in FIG. 2, the icon 230 may represent access to a records database so that a patient's records may be imported into the layout. The icon 231 may represent access to a notes database so that a previously taken note may be imported into the layout. The icon 231 may also include the functionality of enabling the viewer (e.g., creator of the layout or viewer) to import a new note into the layout. The icon 232 may represent access to an images database enabling a viewer to import one or more medical images into the layout. The icon 233 may represent access to a database storing one or more templates of layouts. In some embodiments, a viewer may select an initial layout template, or change layout templates through the icon 233. The icons 234-237 may enable a viewer to step through steps taken to adjust a medical image. For example, assuming the medical image 212 is selected, the icon 234 may enable the viewer to return to the initial, unadjusted state of medical image 234; the icon 235 may enable the viewer to return to one step prior to the current adjusted state (e.g., return to the previous zoom level, or decrease the brightness level); the icon 236 may enable the viewer step forward to a next step in the adjusted step; and the icon 237 may enable the viewer to return to final adjusted state when the snapshot was saved (in such an embodiment, it is assumed that in order to use the icons 236-237, one or more of the icons 234-235 were previously used by the viewer).

The icon 238 may represent access to one or more snapshot features such as saving the state of the layout (e.g., generating a snapshot), naming the snapshot (the particular state) and/or assigning the snapshot (or particular state) to a specified collection. The icon 239 may enable the creator, or viewer, to lock the user interactive display screen 210 such that no adjustments can be made to one or more display areas of the current saved state unless the user interactive display screen 210 is unlocked (e.g., via a password). The icon 240 may represent access to a help guide or a settings menu.

The state in which the user interactive display screen 210 is opened may be a configurable setting. For example, a user may configure the display control logic, (discussed below), to render the medical compilation (e.g., the study) at a predefined state when the medical compilation is selected. In one embodiment, the latest saved state may be automatically rendered when the medical compilation is selected. In a second embodiment, the first saved state may be automatically rendered when the medical compilation is selected.

Figure 3:
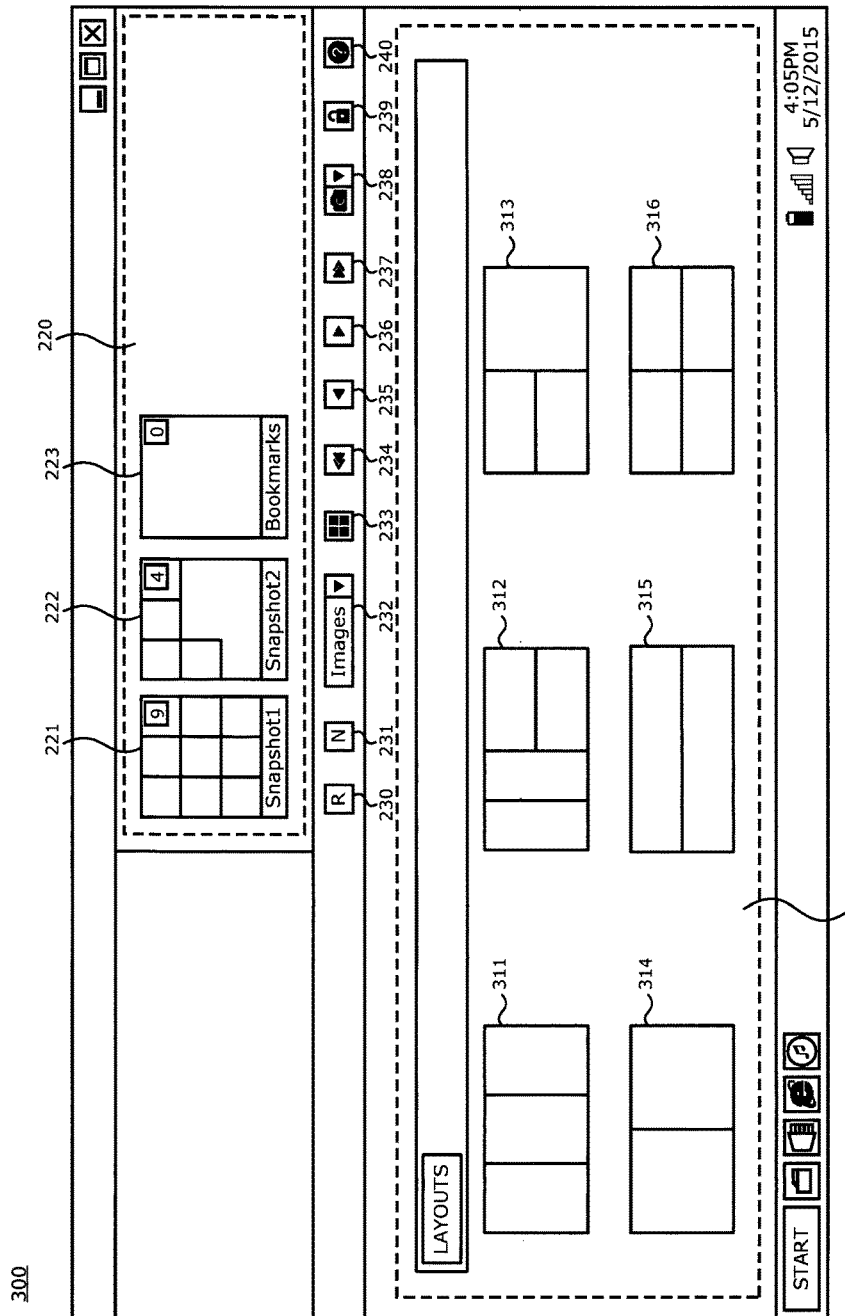
FIG. 3 is an exemplary display layout template selection screen that lists potential display layout templates that are selectable by a user for snapshot generation.

Referring to FIG. 3, an exemplary layout template selection screen that lists potential layout templates that are selectable by a user for user interactive display screen generation is shown. The display screen 300 includes at least the history display area 220 and the icons 230-240 as discussed in FIG. 2. Additionally, the display screen 300 includes a layout templates display screen 310 that includes one or more layout templates that a user may select while creating a layout, which is in turn saved as a snapshot (or state thereof).

For example, the layout templates display screen 310 includes layout templates 311-316. Each of the layout templates 311-316 includes a varied layout for one or more medical images, notes, records, or other information or data that may be relevant to a doctor's examination or review. In one embodiment, a user may have obtained a first piece of data (e.g., a first medical image) that the doctor wishes to compare with a second medical image that will be taken in the near future as well as notes regarding both medical images. The doctor may select a layout template, for example the layout template 316, in order to import the first medical image and notes pertaining to the first medical image. Subsequently, when the second medical image is obtained, the doctor may import the second medical image into the layout template 316 as well as notes pertaining to the second medical image. Therefore, selection of a layout template 311-316 allows a doctor, nurse and/or medical technician to easily place medical data into a layout that promotes ease of viewing, and that can be saved as a snapshot or a state thereof for future reference.

Additionally, display control logic, discussed below, may include logic for generating templates based on a user creating one or more templates. In one embodiment, a user may alter a layout template to include one or more additional display areas, or remove one or more display areas. For example, a user may select the layout template 311 and upon attempting to import a fourth piece of medical data, the control display logic may import the fourth piece of medical data into a fourth display area, splitting one display area into two, or condensing the current display areas and adding a fourth display area. Upon altering a layout template, the display control logic may add the newly created layout to the layout templates of display area 310. In another embodiment, the user may be prompted as to whether the altered layout is to be added to the layout templates of the display area 310.

II. Accessing Snapshots from a Home Screen

Figure 4:
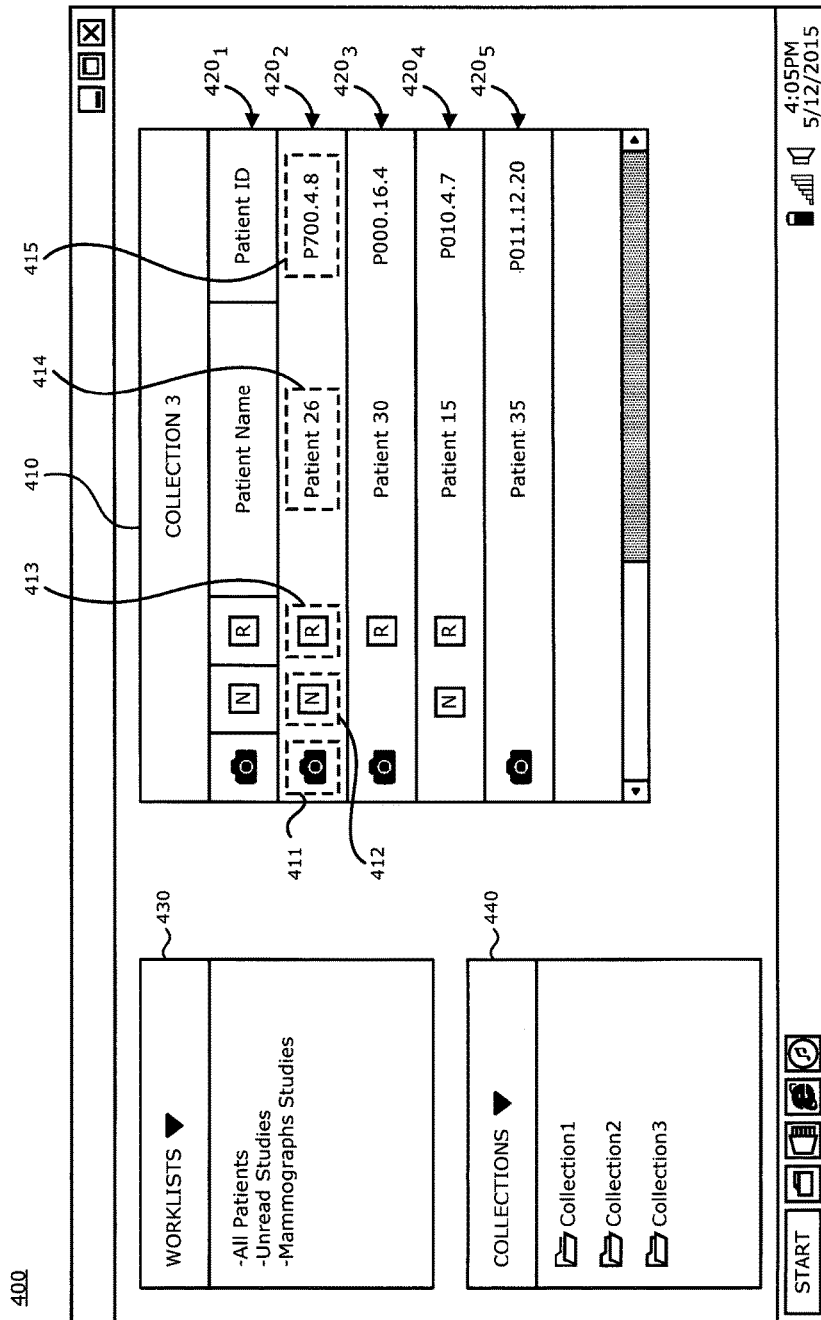
FIG. 4 is an exemplary display screen that illustrates a worklists display area, a collections display area and a listing of studies within a collection.

Referring to FIG. 4, an exemplary display screen that illustrates a worklists display area, a collections display area and a listing of studies within a collection is shown. In one embodiment, the display screen 400 may represent a "home" screen providing access to a plurality of studies, worklists, collections and/or or individual snapshots, or states thereof. Herein, the display screen 400 includes a display area 410, a worklists display area 430 and a collections display area 440.

The worklists display area 430 and the collections display area 440 recite worklists and collections, respectively. The term "worklist" refers to a rule-based grouping of studies while the term "collection" refers to a grouping of studies manually assembled by a user. The embodiment in FIG. 4 illustrates three current worklists, "All Patients," "Unread Studies," and "Mammographs Studies." Therefore, for example, all studies (e.g., snapshots, medical images, notes, etc.) that have not been opened may be automatically placed in the worklist titled, "Unread Studies," based one or more rules. Additionally, for example, the worklist titled, "Unread Studies," may also include studies that have not been finalized. With a worklist, a viewer or user is not required to manually add data (e.g., a snapshot, a state of a snapshot, a medical image, etc.) to a worklist grouping, instead, logic, stored on a non-transitory computer-readable medium of an electronic apparatus will automatically add the data to the appropriate worklist. Examples, of the electronic apparatus may include a desktop computer, a tablet, a laptop, a "smart" mobile phone, or a dedicated server. Similarly, the logic may remove a study from a worklist according to one or more rules (e.g., a study will be removed from the worklist "Unread Studies" when the study is opened, assuming a rule of the worklist, "Unread Studies," is to place all unopened, e.g., unread, studies into the worklist).

In contrast, studies are added to, or removed from, a collection only when done so manually by a user or viewer. It is envisioned that a combination of a worklist and collection grouping may be implemented wherein a user may manually add to, or remove from, the grouping but also establish rules for automatic addition and removal. Although FIG. 4 illustrates only three worklists and three collections, more or less worklists and/or collections may be provided or created.

As is seen FIG. 4, the studies of "Collection 3" are listed in the display area 410, wherein the exemplary rows 4201-4205 are illustrated. The row 4201 includes headers for each column of the rows 4202-4205. For example, the row 4202 may include icons in one or more columns including the icon 411 indicating the presence of a snapshot for the corresponding study of row 4202, the icon 412 indicating the presence of notes (e.g., by a nurse or doctor) for the corresponding study of row 4202, the icon 413 indicating the presence of a medical record corresponding to the study of row 4202. Additionally, a patient name 414 and a patient identification (ID) 415 corresponding to the study of row 4202 may be included. Furthermore, more or less columns and/or rows may be present in the display area 410 than are illustrated in FIG. 4. In one embodiment, the icon 411 may include an icon indicating a number of states available in the snapshot (e.g., as was discussed with the snapshots 221 and 222 in the history display area 220 of FIG. 2).

Figure 5:
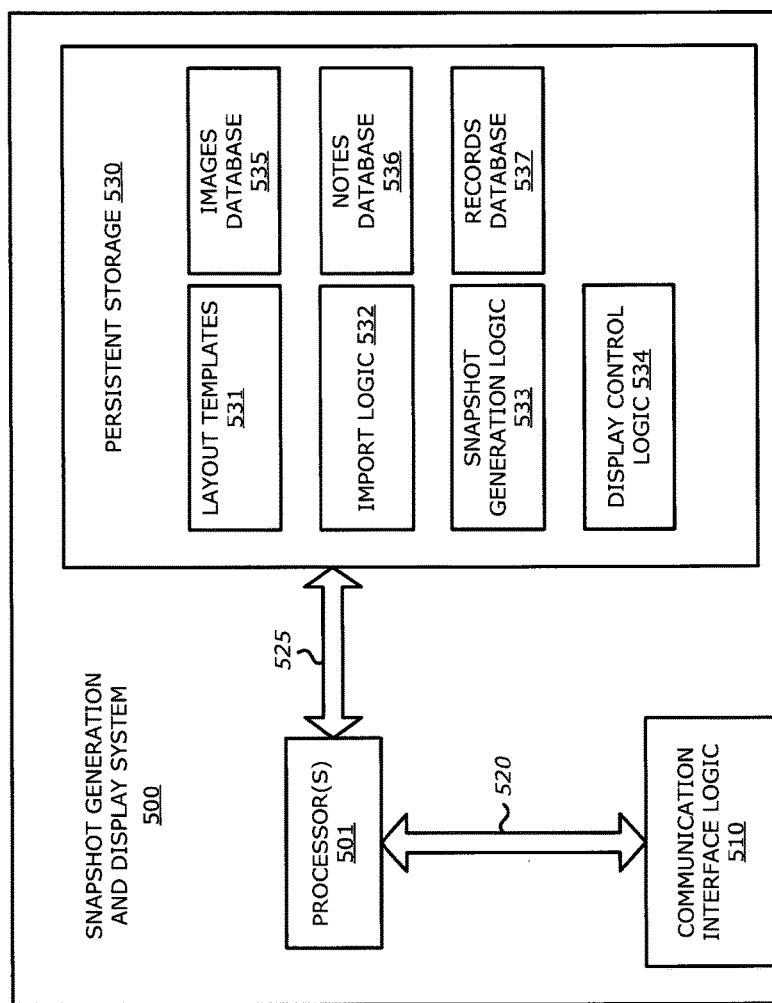
FIG. 5 is an exemplary embodiment of a logical representation of a snapshot generation and display system that generates and renders the displays of FIGS. 2-4.

Referring now to FIG. 5, an exemplary embodiment of a logical representation of a snapshot generation and display system 500 that generates and renders the displays of FIGS. 2-4 is shown. The snapshot generation and display system 500 includes one or more processors 501 that are coupled to communication interface logic 510 via a first transmission medium 520. The communication interface logic 510 enables communications with other electronic devices, specifically enabling communication with remote users such as doctors, nurses and/or medical technicians. According to one embodiment of the disclosure, communication interface logic 510 may be implemented as a physical interface including one or more ports for wired connectors. Additionally, or in the alternative, communication interface logic 510 may be implemented with one or more radio units for supporting wireless communications with other electronic devices.

The processor(s) 501 is further coupled to persistent storage 530 via transmission medium 525. According to one embodiment of the disclosure, persistent storage 530 may include (a) the layout templates 531, (b) an import logic 532, (c) a snapshot generation logic 533, (d) a display control logic 534, (e) an images database 535, (f) a notes database 536 and (g) a records database 537. The import logic 532 may include logic for retrieving one or more pieces of information from a storage device and importing each of the one or more pieces of information into a separate display area of a layout template. For example, the pieces of information may include, but are not limited or restricted to, (i) medical images, including x-rays, mammograms, computerized tomography (CT) scans, magnetic resonance imaging (MRI), positron emission tomography (PET) scan and/or ultrasound imaging, (ii) physician's notes regarding one or more of the medical images and/or (iii) medical records corresponding to one or more of the subjects of the one or more medical images.

The snapshot generation logic 533 may include logic for saving at least a first state of the layout template. Saving the first state may include storing, at least, (i) the one or more pieces of information, and (ii) viewing properties of each of the one or more pieces of information in a non-transitory computer-readable medium. The display control logic 534 may include logic for retrieving one of a set of saved states of the layout template for display according to a selection of a user and displaying (e.g., rendering a display screen) the retrieved one of the set of saved states of the layout template. Additionally, the display control logic 534 may include logic for adjusting one or more of the viewing properties according to instructions by the user (e.g., altering a brightness level, a zoom level, a contrast level, etc.). Furthermore, the display control logic 534 may include logic for stepping back in a series of adjustments made to one or more pieces of information included in a snapshot (or state thereof). In one embodiment, the display control logic 534 may, according to instructions received via the user selecting various icons on the display screen, step back to previous states based on adjustments to one or more viewing properties.

For example, assume a doctor had increased the brightness level from 100% to 150% and then increased the zoom level from to focus on a particular aspect of the medical image before saving the state of the layout as a first state of a snapshot and closed the display screen. Upon opening the first state of the snapshot, the doctor (or another user) would see the medical image at a brightness level of 150% and at the increased zoom level focusing on the particular aspect of the medical image. The doctor may then step back to previous states based on the adjustments to the medical image that were previously made. Therefore, the doctor may step back to a normal zoom level and subsequently step back to a brightness level of 100% (e.g., by selecting icon 235 of FIG. 2, for example). Additionally, the doctor may be able to return to the initial state of the medical image (e.g., by selecting icon 234 of FIG. 2, for example), step forward, assuming a step back has been taken (e.g., by selecting icon 236 of FIG. 2, for example) and/or step forward to the state when the first state was saved (e.g., by selecting icon 237 of FIG. 2, for example). Of course, when implemented as hardware, one or more of these logic units could be implemented separately from each other.

The images database 535, the notes database 536 and the records database 537 may comprise a single non-transitory computer-readable medium storage device or may each be a separate non-transitory computer-readable medium storage device. In one embodiment, each of the databases 535-537 may take the form of a hash table on a single non-transitory computer-readable medium storage device. The images database 535 stores medical images that a user may import into a display area of a layout template. The notes database 536 stores notes recorded by a doctor, nurse, medical technician, etc., that a user may import into a display area of a layout template. Finally, the records database 537 stores medical records that a user may import into a display area of a layout template.

a. Snapshot Generation Process

Figure 6:
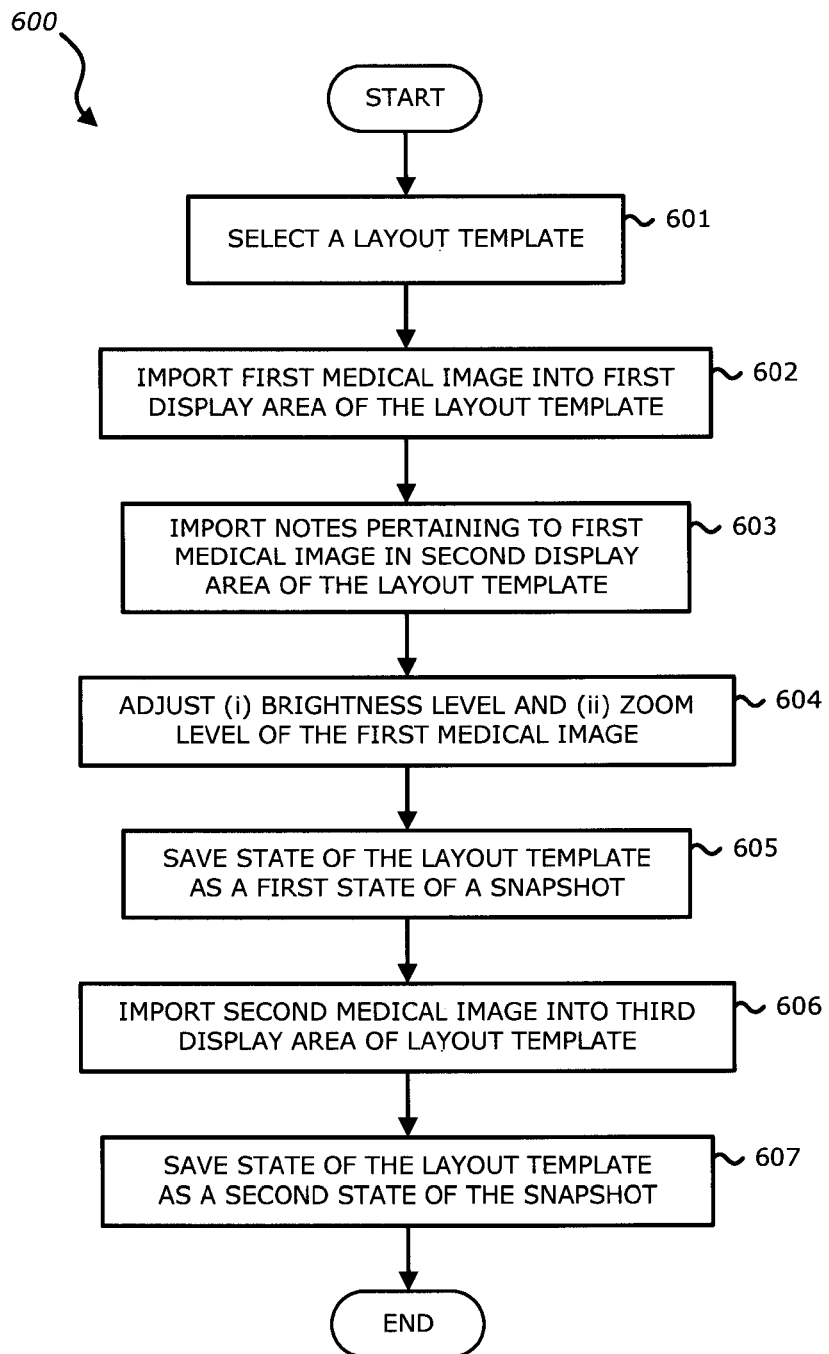
FIG. 6 is a flowchart of an example process of generating a snapshot having a first state and a second state.

Referring to FIG. 6, a flowchart of an example process of generating a snapshot having a first state and a second state is provided. Each block illustrated in FIG. 6 represents an operation performed in the method 600 of generating a snapshot including a first and second state. At block 601, a layout template is selected from one or more pre-constructed templates. For example, referring to FIG. 3, a doctor may select one of the layout templates 311-316 shown in the display area 310. Following the selection of a layout template, a first medical image is imported into a first display area of the layout template (block 602). In one embodiment, the doctor may have taken a plurality of x-ray images of a patient and may select a first x-ray image to import into the layout template. For example, the first x-ray image may show an injury of a patient from a first perspective.

At block 603, the doctor may import notes pertaining to the imported first medical image in a second display area of the layout template. For example, a doctor may have previously recorded notes while taking the x-ray images. Alternatively, or in addition to, the doctor may enter notes in the second display area while examining the first medical image.

At block 604, the doctor may adjust one or more viewing properties of the first medical image, such as, among others, (i) a brightness level and/or (ii) a zoom level of the first medical image. In such an example, the doctor may adjust a brightness level in order to more clearly examine the first medical image. In addition, the doctor may increase the zoom level of the medical image in order to focus the examination on a particular portion of the first medical image, e.g., one of a plurality of broken bones suffered during a car accident, wherein the one particular bone will be the focus of a first surgery.

Subsequent to importing the first medical image and notes pertaining to the first medical image (or recording notes during examination of the first medical image) and adjusting one or more viewing properties of the first medical image, the doctor may save the state of the layout template as a first state of a snapshot (block 605). As discussed above, the doctor may save the state of the layout template such that (i) the specific arrangement of medical images, notes, medical records, etc., is saved and (ii) any adjustments made to the viewing properties (e.g., display attributes) of the medical images are preserved. Therefore, in this example, the adjustment of the brightness level and the zoom level would be persevered. The saved state of the layout template may be referred to as a first state of the snapshot. As discussed above, it is advantageous to save a state of the layout because it is difficult for a doctor to recall the exact steps of obtaining the state from which a conclusion regarding an injury or course of treatment was drawn. Additionally, a saved state of a layout is easy to transmit to a second doctor and/or a nurse or medical technician located remotely compared to transmitting the medical information and instructions as to obtaining the desired state of the layout.

After saving the first state of the snapshot, the doctor may import a second medical image into a third display area of the layout template (block 606). In one embodiment, a second medical image may be a second perspective of the injury on which the first medical image is focused. Alternatively, the second medical image may be the same x-ray as the first medical image with its viewing properties adjusted differently than the first medical image, an x-ray of a second injury, an x-ray of a second patient having undergone a successful surgery to correct the injury on which the first medical image is focused, etc. Although the method 600 states that a second medical image is imported into the third display area of the layout template, the doctor may import medical records of the patient of whom the first medical image depicts or other medical information (e.g., treatment or surgery protocol, a timeline for treatment, etc.).

At block 607, the doctor may then save the state of the layout template as a second state of the snapshot. Having a plurality of saved states may be advantageous as a doctor may use a first state to discuss the injury and potential treatment options with a second doctor or surgeon and use a second state to discuss the injury and potential treatment options with a nurse and the patient as a second doctor or surgeon may not desire to have the additional information that is shown to a nurse or the patient (or vice versa). For example, a second doctor may not want to see an x-ray of a successful surgery to correct the injury but may only need to see one or more perspectives of the actual injury. In the same example, a doctor may find it easier to explain the upcoming surgery to the patient by showing an x-ray of a successful surgery next to an x-ray of the injury (e.g., to explain that a metal plate will be inserted during surgery and what the result will be).

Any combination of the above features and functionalities may be used in accordance with one or more embodiments. In the foregoing specification, embodiments have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction.

What is claimed is:

1. A method comprising:
receiving a selection of a template, from a plurality of templates available for selection, the selected template comprising at least a first display area and a second display area;
receiving a first selection of: (i) first information and (ii) a first display area of the template;
receiving a second selection of: (i) second information and (ii) a second display area of the template;
generating an interactive display of a medical information compilation, the interactive display comprising the first information in the first display area and the second information in the second display area;
saving a first state of the interactive display, wherein the first state is persisted and comprises first values of a plurality of display attributes of the first information and the second information, and
wherein the plurality of display attributes of the first information and the second information are editable and the first information and the second information each include one of (i) a medical image, (ii) medical notes, or (iii) a medical record;
responsive to an editing event, editing a first display attribute of the plurality of display attributes; and
saving a second state of the interactive display including the edited first display attribute of the plurality of display attributes, wherein the saved second state is persisted; and
generating a second interactive display of the medical information compilation comprising the first display area and the second display area, and inserting a third area, the third area displaying a representation of a snapshot of the user-selected template, the snapshot including the saved, persisted first and second states, such that the user can recall for display each of the first and second states of the snapshot.

2. The method of claim 1 wherein the plurality of display attributes includes zoom level, brightness level, and contrast level.

3. The method of claim 1, wherein the plurality of display attributes of the first information include one or more successive steps of adjustments to the first information, and wherein each of the one or more steps of adjustments to the first information are selectable for display.

4. The method of claim 3, wherein the plurality of display attributes of the second information include one or more successive steps of adjustments to the second information, and wherein each of the one or more steps of adjustments to the second information are selectable for display.

5. The method of claim 1 further comprising:
responsive to an editing event,
adding a fourth display area to the interactive display,
receiving a third selection of third information,
importing the third information into the fourth display area; and
saving, as a third state, display layout, wherein the interactive display includes the fourth display area.

6. The method of claim 5 further comprising:
creating a second template according to the interactive display, wherein the second template includes the first display area, the second display area, the third display area, and the fourth display area.

7. The method of claim 1, wherein selecting the template is done through the selection of the template from a plurality of saved templates from a graphic user interface.

* * * * *